US012702594B2

(12) United States Patent
Miller et al.

(10) Patent No.: US 12,702,594 B2
(45) Date of Patent: Aug. 11, 2026

(54) ADHESIVE NITRIC OXIDE DELIVERY BANDAGE FOR SKIN CONDITION HEALING

(71) Applicant: NOxy Health Products, Inc., San Mateo, CA (US)

(72) Inventors: C. Michael Miller, Anaconda, MT (US); David A. Bell, Farmington, UT (US)

(73) Assignee: NOXY HEALTH PRODUCTS, INC., Anaconda, MT (US)

( * ) Notice: Subject to any disclaimer, the term of this patent is extended or adjusted under 35 U.S.C. 154(b) by 185 days.

(21) Appl. No.: 18/459,568

(22) Filed: Sep. 1, 2023

(65) Prior Publication Data

US 2024/0074908 A1 Mar. 7, 2024

Related U.S. Application Data

(60) Provisional application No. 63/403,180, filed on Sep. 1, 2022.

(51) Int. Cl.

| | |
|---|---|
| ***A61F 13/00*** | (2024.01) |
| ***A61K 9/70*** | (2006.01) |
| ***A61L 15/24*** | (2006.01) |
| ***A61L 15/44*** | (2006.01) |
| ***A61M 35/00*** | (2006.01) |

(52) U.S. Cl.

CPC ........ *A61F 13/00063* (2013.01); *A61K 9/703* (2013.01); *A61L 15/24* (2013.01); *A61L 15/44* (2013.01); *A61M 35/30* (2019.05)

(58) Field of Classification Search

CPC ... A61F 13/00063; A61F 13/05; A61K 9/703; A61L 15/24; A61L 15/44; A61L 2300/114; B32B 23/10; B32B 27/12; B32B 2405/00; B32B 2255/02; B32B 2255/26; B32B 2307/7242; B32B 5/024; B32B 27/304; B32B 27/32; B32B 27/40; A61M 35/30

See application file for complete search history.

(56) References Cited

U.S. PATENT DOCUMENTS

| | | | | |
|---|---|---|---|---|
| 9,522,260 B2 * | 12/2016 | Mutus | A61K 31/095 | |
| 2008/0097282 A1 * | 4/2008 | Hole | A61K 33/00 | 604/23 |
| 2008/0255535 A1 * | 10/2008 | Yoshikawa | A61J 1/2093 | 604/416 |
| 2013/0330244 A1 * | 12/2013 | Balaban | A61P 15/00 | 422/236 |

FOREIGN PATENT DOCUMENTS

| | | | | |
|---|---|---|---|---|
| EP | 2533773 B1 | | 8/2015 | |
| GB | 2567844 A | * | 5/2019 | A61M 16/12 |
| WO | WO-9620040 A1 | * | 7/1996 | B01D 69/108 |
| WO | WO-0074616 A1 | * | 12/2000 | A61K 9/7084 |
| WO | 2021198470 A1 | | 10/2021 | |

OTHER PUBLICATIONS

International Search Report for PCT/US2023/073266 mailed Nov. 27, 2023, 4 pages.

* cited by examiner

*Primary Examiner* — Susan S Su

(74) *Attorney, Agent, or Firm* — Honigman LLP; Heidi Berven; David J. Thomas

(57) ABSTRACT

An adhesive bandage that is capable of delivering nitric oxide gas to skin is generally disclosed. The bandage may be used for topical skin therapy of a patient, such as, for example, to promote healing of a wound or condition, or to provide exogenous nitric oxide supplementation.

20 Claims, 6 Drawing Sheets

ADHESIVE NITRIC OXIDE DELIVERY BANDAGE FOR SKIN CONDITION HEALING

CROSS-REFERENCE TO RELATED APPLICATIONS

This U.S. patent application claims priority under 35 U.S.C. § 119(e) to U.S. Provisional Application 63/403,180, filed on Sep. 1, 2022. The disclosure of this prior application is hereby incorporated by reference in its entirety.

TECHNICAL FIELD

The present disclosure relates generally to an adhesive bandage that is capable of delivering nitric oxide to a wound on the skin. The bandage can be used for topical skin therapy of a patient, such as, for example, to promote healing of a condition or wound, or to provide exogenous nitric oxide supplementation.

BACKGROUND

Adhesive bandages are one of the most commonly used tools to treat wounds on the skin. They protect wounds from infection, and they promote healing. Antibacterial agents are often incorporated into wound dressings to treat and prevent infection. However, many pathogens have now developed resistance to commonly used antibiotics, limiting the effectiveness of some topically administered antibacterial agents. In addition, while antibacterial agents kill pathogens, they may also damage healthy tissue and impede the wound healing process. Finally, some patients are allergic to commonly used antibacterial agents.

Nitric oxide gas represents one alternative to antibacterial agents for the treatment of skin wounds. Nitric oxide, or nitrogen monoxide, is a colorless gas that has the molecular formula NO. In mammals, including humans, nitric oxide is considered a "signaling molecule" in many physiological processes. It is a key vertebrate biological messenger, playing a role in a variety of biological processes. As a messenger molecule, nitric oxide transmits signals to cells in the cardiovascular, nervous, and immune systems. Nitric oxide is a free radical. As a free radical, nitric oxide is much more reactive than other signaling molecules. The small molecular size of nitric oxide enables it to diffuse through cell membranes and walls to perform a range of signaling functions in various bodily systems.

Nitric oxide is biosynthesized endogenously from oxygen, L-arginine, and nicotinamide adenine dinucleotide phosphate (NAPH) by various nitric oxide synthase (NOS) enzymes. Reduction of inorganic nitrate and/or nitrite may also produce nitric oxide. Nitric oxide is an endothelium-derived relaxing factor. The endothelium, or inner liner, of blood vessels uses nitric oxide to signal to surrounding smooth muscle to relax, which results in vasodilation and increased blood flow. Nitric oxide's role in dilating blood vessels makes it an important controller of blood pressure. Nitric oxide is also produced by neurons and is used by the nervous system as a neurotransmitter to regulate functions ranging from digestion to blood flow to memory and vision. In the immune system, nitric oxide is produced by macrophages, which are a type of leukocyte that engulfs bacteria and other foreign particles that have invaded the body. The nitric oxide released by macrophages kills bacteria, other parasites, and tumor cells by disrupting their metabolism.

As people age, their ability to naturally produce nitric oxide diminishes. By the age of 50, a person's natural ability to produce nitric oxide may decrease by approximately 50%. As a result, researchers have focused on devising nitric oxide supplementation compositions and methods.

Delivering nitric oxide to where it is needed in patients has been an ongoing challenge. Nitric oxide is a gas at ambient temperature and atmospheric pressure, and it has a short half-life under physiologic conditions. Controlled delivery of nitric oxide for a given therapeutic use is also important from a therapeutic standpoint because release of controlled amounts of nitric oxide may lead to desirable therapeutic effects such as the formation of healthy tissue and decreases in inflammation. Thus, what is needed is a bandage that is capable of delivering nitric oxide to the skin in a controlled and safe fashion.

SUMMARY

These and other needs are met by the present disclosure, which is directed to an adhesive bandage for delivering nitric oxide gas to a skin wound or condition in a controlled and safe fashion.

The present disclosure comprises an adhesive bandage which is equipped with two chambers of suitable shape having flexible surfaces that are collapsible when crushed or squeezed. The chambers contain chemicals that, when mixed, form nitric oxide gas. Thus, the first chamber contains a mixture comprising water and a mild acid and a second chamber contains a mixture comprising water and a source of nitric oxide.

The contents of the first and second chambers are then put into contact in a center mixing chamber which is situated between the first and second chambers. The mixing chamber is equipped with a surface that sits against the skin that comprises a gas permeable membrane that allows for the diffusion of small molecules such as nitric oxide gas from the mixing chamber to the skin. The diffusible surface is typically a membrane that has sufficient pore sizes and that is derived from a thermoplastic polymer such as polytetrafluoroethylene. In some examples, the material is a material such as Gore-Tex®.

When pressure is exerted on the first and second chambers, passageways between the first and second chambers to the middle mixing chamber are forced open so that their contents enter and are allowed to mix in the mixing chamber. Nitric oxide gas, which is formed upon mixing of the contents of the first and second chambers, diffuses out of the mixing chamber through the membrane to contact the skin.

Thus, in one aspect, an adhesive bandage for delivering nitric oxide gas to skin comprises a first chamber containing a first mixture, a second chamber containing a second mixture that, when mixed with the first mixture, forms nitric oxide gas, and a mixing chamber disposed between the first chamber and the second chamber and configured to receive the first mixture and the second mixture to form nitric oxide gas. This aspect includes one or more of the following optional features.

The first chamber may be connected to the mixing chamber by a first rupturable gateway. The second chamber may be connected to the mixing chamber by a second rupturable gateway. When fingertip pressure is applied to the first and second chambers, the first and second gateways may rupture, allowing for mixing of the contents of the first and second chambers in the mixing chamber to form nitric oxide gas.

In some implementations, the adhesive bandage may further comprise a fourth chamber containing a third mixture that is the same as the first mixture and a fifth chamber containing a fourth mixture that is the same as the second mixture. The adhesive bandage may further comprise a bandage layer configured to adhere to the skin, wherein the bandage layer includes a membrane configured to diffuse the nitric oxide gas from the mixing chamber to the skin. The membrane may allow only nitric oxide gas to pass through the membrane.

The first chamber may be connected to the mixing chamber by a first passageway including a first plug. The second chamber may be connected to the mixing chamber by a second passageway including a second plug. When fingertip pressure is applied to the first and second passageways, the first and second plugs may move toward the mixing chamber, allowing for mixing of the contents of the first and second chambers in the mixing chamber to form nitric oxide gas.

In another aspect, an adhesive bandage for delivering nitric oxide gas to skin comprises a first chamber containing a first mixture, a second chamber containing a second mixture that, when mixed with the first mixture, forms nitric oxide gas, a mixing chamber disposed between the first chamber and the second chamber and configured to receive the first mixture and the second mixture to form nitric oxide gas, and a bandage layer disposed underneath the first, second, and mixing chambers, the bandage layer including a membrane configured to diffuse the nitric oxide gas from the mixing chamber to the skin. This aspect includes one or more of the following optional features.

The first chamber may be connected to the mixing chamber by a first rupturable gateway. The second chamber may be connected to the mixing chamber by a second rupturable gateway. When fingertip pressure is applied to the first and second chambers, the first and second gateways may rupture, allowing for mixing of the contents of the first and second chambers in the mixing chamber to form nitric oxide gas.

The membrane may allow only nitric oxide gas to pass through the membrane.

The first chamber may be connected to the mixing chamber by a first passageway including a first plug. The second chamber may be connected to the mixing chamber by a second passageway including a second plug. When fingertip pressure is applied to the first and second passageways, the first and second plugs may move toward the mixing chamber, allowing for mixing of the contents of the first and second chambers in the mixing chamber to form nitric oxide gas.

In another aspect, a method for creating an adhesive bandage for delivering nitric oxide gas to skin comprises providing a filling block including a first cavity, a second cavity, and a third cavity, providing a membrane layer over the filling block, the membrane layer including a first chamber disposed in the first cavity, a second chamber disposed in the second cavity, and third chamber disposed in the third cavity, filling the first cavity with a first mixture, filling the third cavity with a second mixture, wherein the first mixture, when mixed with the second mixture in the second chamber, forms nitric oxide gas. This aspect includes one or more of the following optional features.

The method may further comprise applying a transmission layer to the membrane layer, applying a bandage layer to the membrane layer to create the adhesive bandage, and removing the adhesive bandage from the filling block.

The proposed adhesive bandage may have the following structure and may be used in the manner stated below.

BRIEF DESCRIPTION OF THE DRAWINGS

FIG. 6 is a graph illustrating NO production for a first exemplary test using liquid and liquid reactants; and FIG. 7 is a graph illustrating NO production for a second exemplary test using liquid and powder reactants.

DETAILED DESCRIPTION

The foregoing and other objects and features of the present disclosure will become more fully apparent from the following description and appended claims, taken in conjunction with the accompanying drawings, data, and/or charts. Understanding that these depict only typical embodiments of the present disclosure and are, therefore, not to be considered limiting of its scope.

Figure 1A:
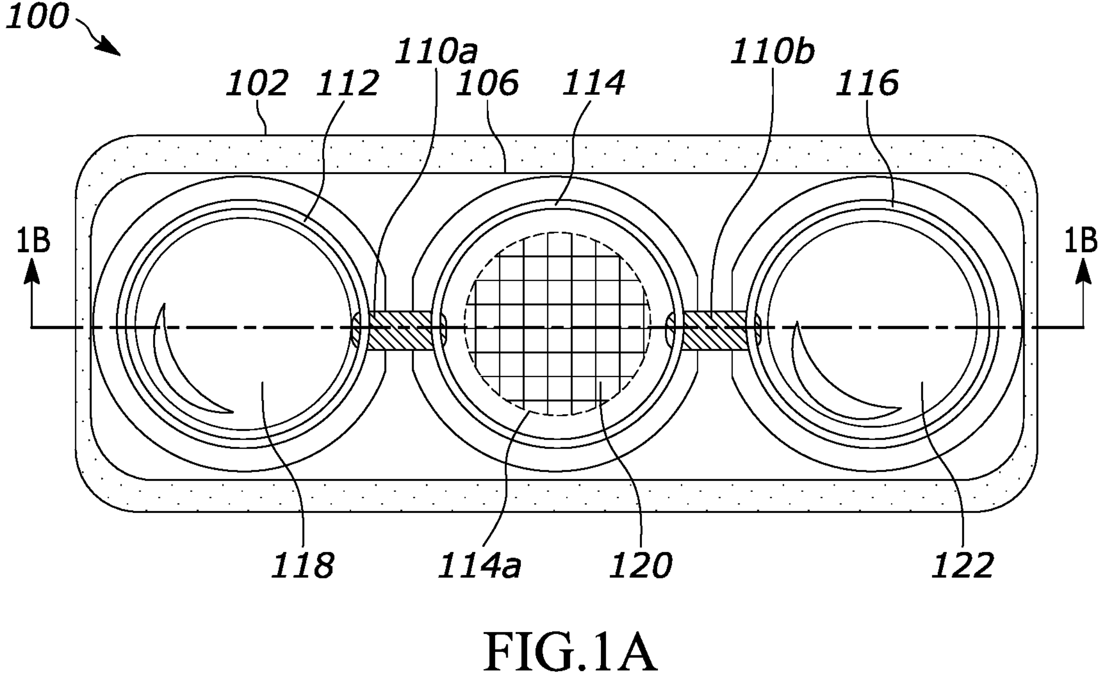
FIG. 1A is a top view of a nitric oxide (NO) delivery bandage, in accordance with the principles of the present disclosure.
Figure 1B:
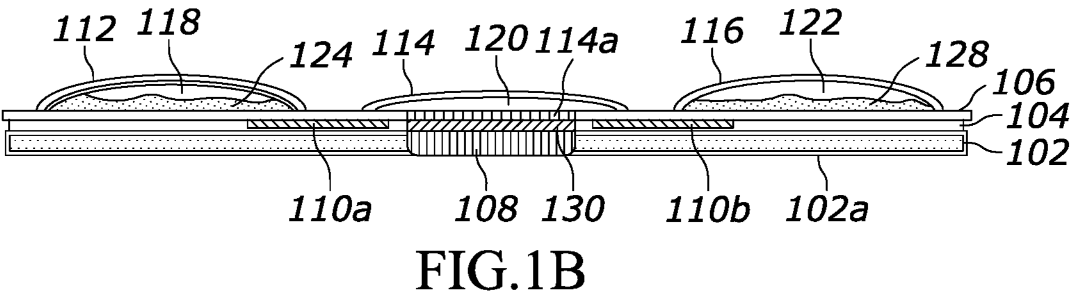
FIG. 1B is a cross-sectional view of the NO delivery bandage of FIG. 1A, taken along lines 1B-1B.
Figure 1C:
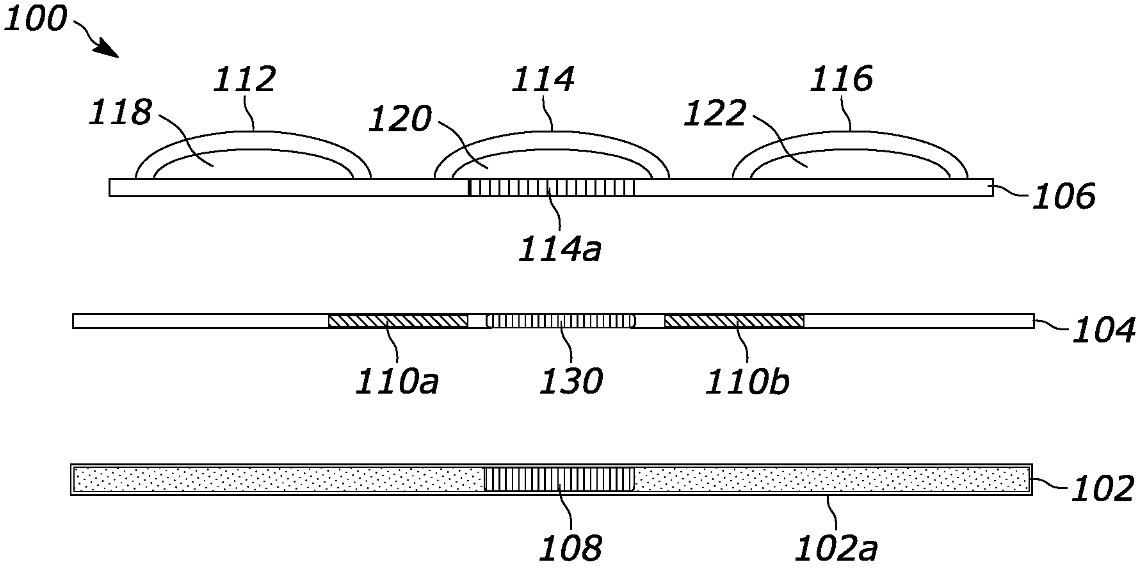
FIG. 1C is an exploded side view of the NO delivery bandage of FIG. 1A.
Figure 2A:
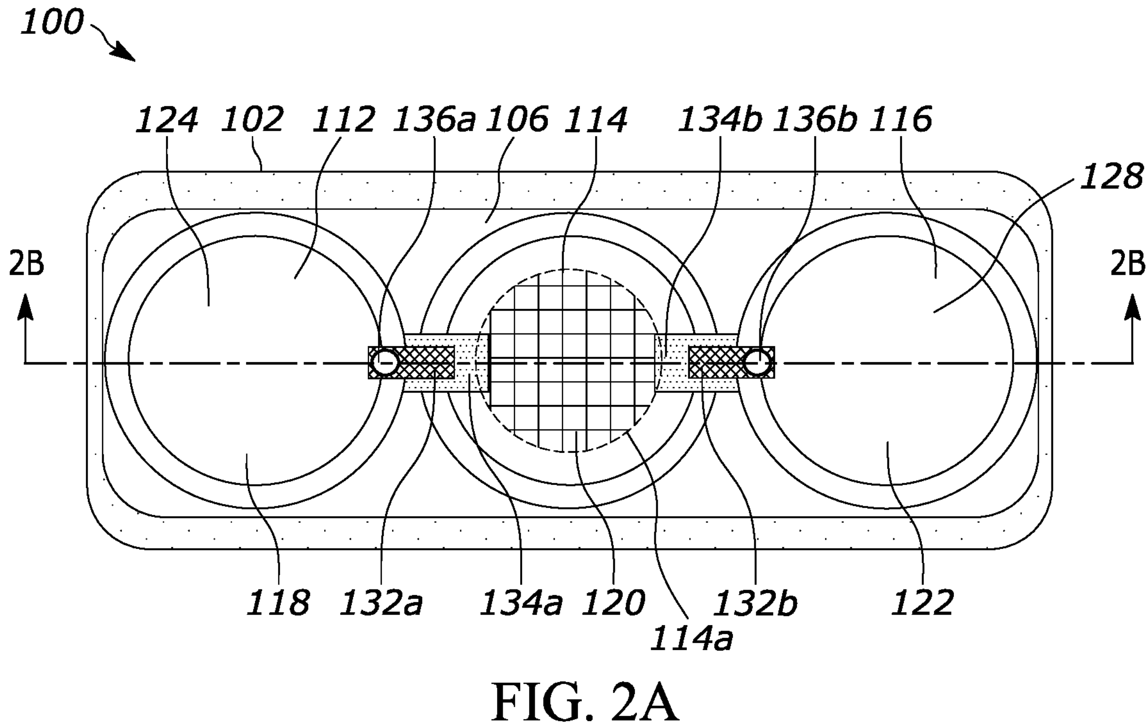
FIG. 2A is a top view of a nitric oxide (NO) delivery bandage with beads in a closed position, in accordance with the principles of the present disclosure.
Figure 2B:
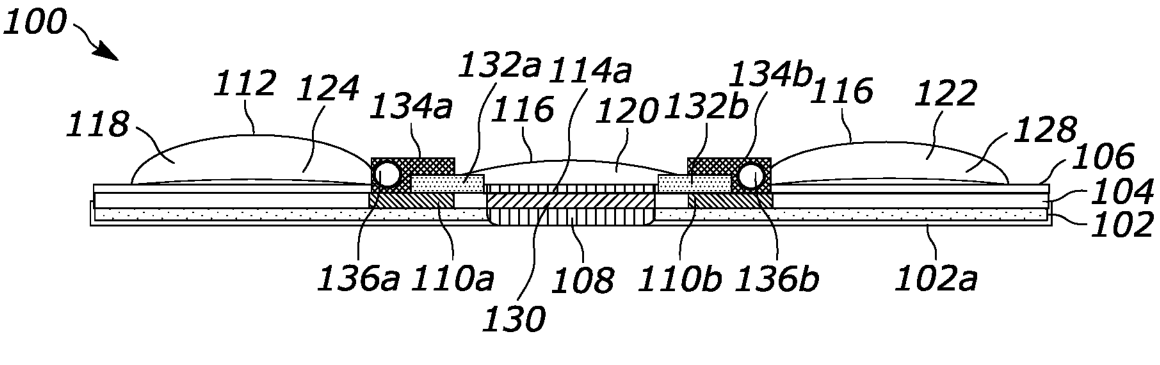
FIG. 2B is a cross-sectional view of the NO delivery bandage of FIG. 2A, taken along lines 2B-2B.
Figures 2C, 2D:
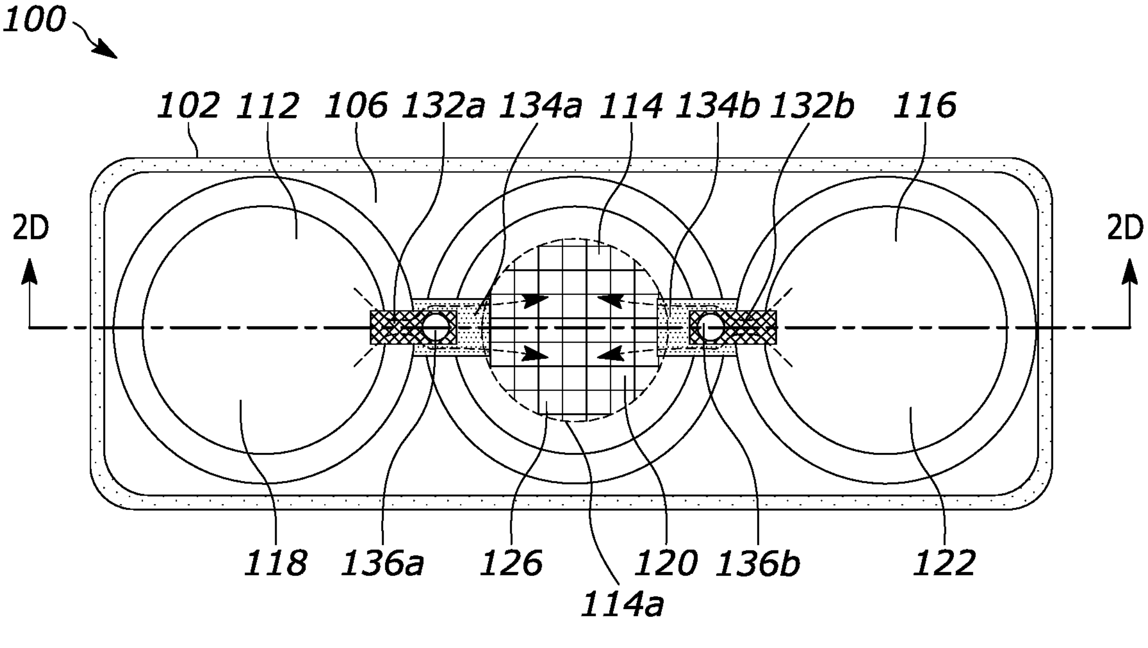
FIG. 2C is a top view of a nitric oxide (NO) delivery bandage with beads in an open position, in accordance with the principles of the present disclosure.
FIG. 2D is a cross-sectional view of the NO delivery bandage of FIG. 2C, taken along lines 2D-2D.

Referring to FIGS. 1A-1C, the present disclosure is directed to a nitric oxide (NO) bandage 100 that delivers nitric oxide gas to a skin wound, skin condition (e.g., acne, rosacea, etc.), and/or inflammation (e.g., psoriasis, arthritis, etc.). The NO bandage 100 includes a bandage layer 102, a transmission layer 104, and a membrane layer 106. The bandage layer 102 has the thickness and flexibility of a skin bandage and is typically fabricated form a woven fabric or a plastic such as polyvinyl chloride, polyethylene, or polyurethane, or latex. The bandage layer 102 includes a bottom surface 102*a* that is coated with adhesive. The adhesive is typically an acrylate such as an acrylate, methacrylate or epoxy diacrylate that sticks to skin. The bandage layer 102 includes a membrane portion 108 configured to permit NO gas to pass through the bandage layer 102. The membrane portion 108 may be designed such that NO gas-only escapes through the membrane portion 108 and into the skin tissue beneath the membrane portion 108.

The transmission layer 104 includes a first transmission portion 110*a* and a second transmission portion 110*b*. In some implementations, the transmission portions 110*a*, 110*b* may be formed from 25% thickness compared to the rest of the transmission layer 104 to permit the transfer of solutions through the transmission portions 110*a*, 110*b*. The transmission layer 104 includes a membrane portion 130 that aligns with the membrane portion 108 of the bandage layer 102.

The membrane layer 106 includes a first bubble 112, a second bubble 114, and a third bubble 116. The second bubble 114 may be disposed between the first bubble 112 and the third bubble 116. The second bubble 114 includes a membrane portion 114*a* that aligns with the other membrane portions 108, 130. The first bubble 112 defines a first chamber 118, the second bubble 114 defines a mixing chamber 120, and the third bubble 118 defines a third chamber 122. The three chambers 118, 120, 122 may be embedded in the membrane layer 106. The membrane layer 106 is made from a plastic that is suitable for use in the treatment of skin conditions or wounds. In one embodiment, the plastic is selected from biopolymers and synthetic polymers and combinations and mixtures thereof. Non-limiting examples of biopolymers (known alternatively as natural polymers) include alginate, dextran, hyaluronic acid (HA), chitosan, cellulose, gelatin, chitin polyurethane, latex, polyvinyl chloride, and polyethylene. Non-limiting examples of synthetic polymers that can be crosslinked with biopolymers for the bandages of the present disclosure include poly(vinyl alcohol) (PVA), poly(lactic-co-glycolic acid) (PLGA), polylactide (PLA), polyglycolic acid (PGA), polyurethanes (PUs), poly(ethylene oxide) (PEO)/poly(ethylene glycol) (PEG), poly(hydroxyethyl methacrylate) (PHEMA), and poly(vinyl pyrrolidone) (PVP).

The chambers 118, 120, 122 can be any shape that is practical to manufacture and can have flexible or crushable domes. For example, in one embodiment, the chambers 118, 120, 122 are round and are capable of holding a specific volume of liquid sufficient to generate a sufficient amount of nitric oxide gas to treat a condition or wound on the skin that is underneath the NO bandage 100 when the NO bandage 100 is applied to the skin of a person or animal that has a skin condition or wound. The mixing chamber 120 in this and other embodiments is also round. The mixing chamber 120 is capable of holding the total volume of liquid from the first chamber 118 and the third chamber 122.

In one embodiment, the first chamber 118 contains a first mixture 124 comprising water and a mild acid having a pKa of 4-6 to provide a pH of the resulting solution of approximately 4 to 6.9. In one embodiment, the weak acid is selected form the group consisting of Aloe vera gel, lidocaine (as the HCl salt), ascorbic acid, citric acid, hypochlorous acid, and salicylic acid. In a further embodiment, the weak acid is citric acid.

The third chamber 122 contains a mixture 128 comprising water and a source of nitric oxide selected from the group consisting of nitrites derived from elements from Group I and Group II of the Periodic Table of the Elements. In a further embodiment, the nitrite is selected form the group consisting of sodium nitrite, potassium nitrite, calcium nitrite, and magnesium nitrite. In a further embodiment, the nitrite is sodium nitrite.

The contents of the first chamber 118 and the third chamber 122 are then put into contact in the mixing chamber 120 which is a mixing chamber that is situated between the first chamber 118 and the third chamber 122. The first mixture 124 of the first chamber 118 and the second mixture 128 of the third chamber 122 mix in the mixing chamber 120 to create nitric oxide gas 126. The second bubble 114 expands to receive the nitric oxide gas 126 created within the mixing chamber 120 and creates a driving force via the elastic properties of the second bubble 114 to force the nitric oxide gas 126 through the membrane portions 108, 114*a*, 130 to the skin.

The membrane portions 108, 114*a*, 130 allow for the diffusion of small molecules such as nitric oxide gas from the mixing chamber 120 to the skin. The membrane portions 108, 114*a*, 130 are typically gas-permeable membranes. In some implementations, the membrane portions 108, 114*a*, 130 have sufficiently small pore sizes. In some embodiments, the pore size of the membrane portions 108, 114*a*, 130 is 1 micron to 5 microns. In a further embodiment, the membrane portions 108, 114*a*, 130 have a pore size of 1.5 to 3 microns. In a further embodiment, the membrane portions 108, 114*a*, 130 have a pore size of 1.5 to 2.5 microns. In a further embodiment, the membrane portions 108, 114*a*, 130 have a pore size of 2 microns. In a further embodiment, the membrane portions 108, 114*a*, 130 are derived from a thermoplastic polymer such as polytetrafluoroethylene. In a further embodiment, the material is a material such as Gore-Tex®.

In some implementations, the mixing chamber 120 may include a powder mixture (e.g., as loose powder or powder formed into a tablet) and the first and third chambers 118, 122 include liquid mixtures that, when combined with the powder mixture, create nitric oxide gas 126 in the mixing chamber 120. In other implementations, the second bubble 114 may be coated with a thin film within the mixing chamber 120 that, when combined with liquid mixtures of the first and third chambers 118, 122, creates nitric oxide gas 126 in the mixing chamber 120.

In some implementations, the mixtures 124, 128 (liquid, powder, or any other suitable mixture) of the first and third chambers 118, 122 may be colored in any suitable manner, e.g., the mixture 124 may be colored blue and the mixture 128 may be colored yellow, such that, when combined to form the nitric oxide gas 126, the resultant liquid in the mixing chamber 120 may form generally green color. This mixing and changing of colors may provide visual confirmation that the mixture was successful.

When pressure is exerted on the first chamber 118 and the third chamber 122, for instance, by applying fingertip pressure, the first chamber 118 and the third chamber 122 rupture so that their contents enter the mixing chamber 120 through entry gateways or portals, such as the transmission portions 110*a*, 110*b*. The reduced thickness of the transmission portions 110*a*, 110*b* is what forms the first and second gateways. There is no adhesive under the mixing chamber 120, so that nitric oxide gas can freely diffuse from the mixing chamber 120 to the skin wound.

The contents of the first chamber 118 and the third chamber 122 mix in the mixing chamber 120, and a chemical reaction ensues that generates nitric oxide gas. In some implementations, the mixing chamber 120 may be a generally clean environment. In an embodiment, at standard temperature and pressure, (25° C., 1 atm), nitric oxide gas forms after about 1 to 30 seconds of mixing. In a further embodiment, nitric oxide gas forms after about 2 to 25 seconds of mixing. In a further embodiment, nitric oxide gas forms after about 3 to 15 seconds of mixing. In a further embodiment, nitric oxide gas forms after about 5 to 15 seconds of mixing.

As nitric oxide gas is generated as a result of the mixing of the contents of the first chamber 118 and the third chamber 122, it diffuses out of the mixing chamber 120 through the membrane portions 108, 130 as a result of the pressure differential and contacts the skin. The diffusion of nitric acid through the membrane portions 108, 130 to the skin starts between approximately 1 to 20 seconds after application of the NO bandage 100 to the skin. As noted above, nitric oxide gas exerts its healing effect by influencing angiogenesis, inflammation, cell proliferation, matrix deposition, and remodeling.

In some implementations, the NO bandage 100 is designed to stay on the skin and deliver its therapeutic effect for 12 to 36 hours, and then can be replaced with another NO bandage 100 as needed, until healing is complete.

The NO bandage 100 of the present disclosure is shelf and storage stable under normal conditions for up to a year.

Referring to FIGS. 2A-2D, the NO bandage 100 may include gateways between the chambers 118, 120, 122 that includes a first passage **132*a* extending from the first chamber 118 partially into the mixing chamber 120. A second passage 132*b* extends from the third chamber 122 partially into the mixing chamber 120. A third passage 134*a* extends from the mixing chamber 120 partially into the first chamber 118. A fourth passage 134*b* extends from the mixing chamber 120 partially into the third chamber 122. The first passage 132*a* intersects with the third passage 134*a* and the second passage 132*b* intersects with the fourth passage 134*b***.

A first plug **136*a* is disposed in, and translatable along, the first passage 132*a*. A second plug 136*b* is disposed in, and translatable along, the second passage 132*b*. In some implementations, the plugs 136*a*, 136*b* may have a generally spherical shape. The plugs 136*a*, 136*b* may be formed from glass, plastic, metal, or any other suitable material. The plugs 136*a*, 136*b* are shown in a closed position in FIGS. 2A and 2B, in which the contents of the first chamber 118 and the third chamber 122 do not diffuse to the mixing chamber 120. The plugs 136*a*, 136*b* are shown in an open position in FIGS. 2C and 2D, in which the contents of the first chamber 118 and the third chamber 122 diffuse to the mixing chamber 120 through the passages 134*a*, 134*b* around the plugs 136*a*, 136*b* as illustrated by the arrows. The plugs 136*a*, 136*b* may be moved from the closed position to the open position by fingertip pressure forcing the plugs 136*a*, 136*b* along the passages 132*a*, 132*b***.

Figure 3:
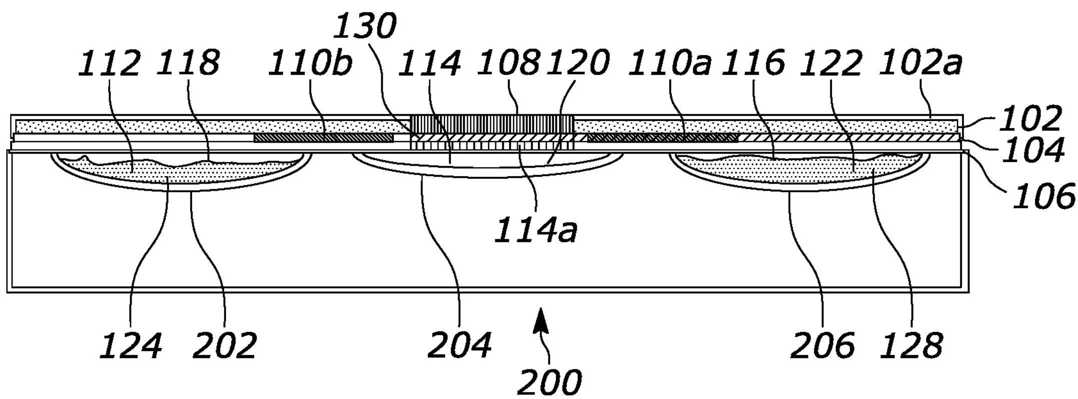
FIG. 3 is a side cross-sectional view of the NO delivery bandage of FIG. 1A including a filling block.

Referring to FIG. 3, a filling block 200 is generally shown that includes a first cavity 202, a second cavity 204, and a third cavity 206. The first cavity 202 corresponds to the first bubble 112. The second cavity 204 corresponds to the second bubble 114. The third cavity 206 corresponds to the third bubble 116. To assemble the NO bandage 100, the membrane layer 206 is placed on the filling block 200 with the bubbles 112, 114, 116 disposed in the cavities 202, 204, 206. Next, a precise volume of acidic solution 124 is placed into the first chamber 118 and a precise volume of nitrite solution 128 is placed in the third chamber 122. Then the transmission layer 104 is applied to the membrane layer 106. Then the bandage layer 102 is applied to the transmission layer 104.

Figure 4:
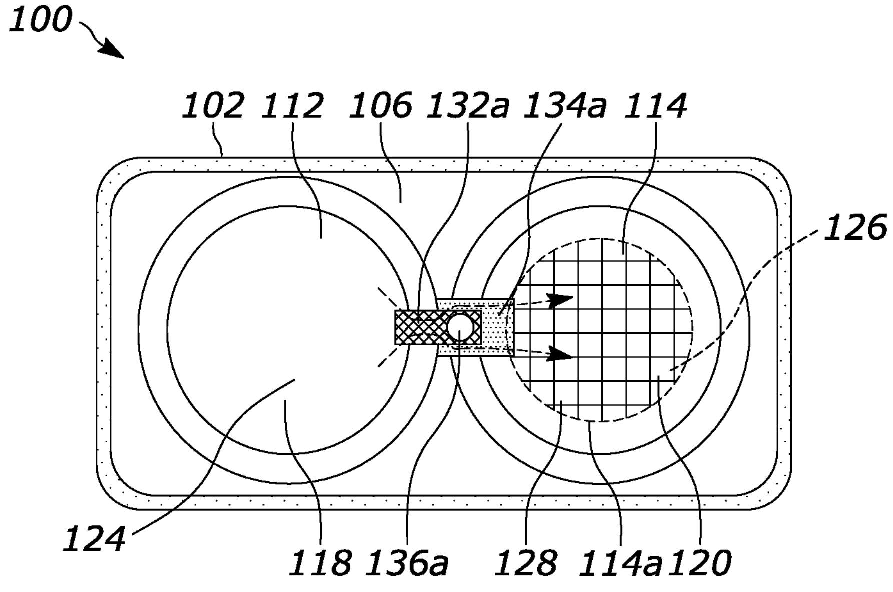
FIG. 4 is a top view of another exemplary nitric oxide (NO) delivery bandage, in accordance with the principles of the present disclosure.

In some implementations, the NO bandage 100 may include any suitable number of bubbles and chambers. For example, referring to FIG. 4, the NO bandage 100 may include the first bubble 112 and the second bubble 114, i.e., only two bubbles and chambers. The first bubble 112 may include the first mixture 124 in the first chamber 118, and the second bubble 114 may include the second mixture 128 in the mixing chamber 120. Thus, when the first mixture 124 enters the mixing chamber 120, e.g., through the passages **132*a*, 134*b* when the plug 136*a* is moved to the open position, the mixtures 124, 128 combine in the mixing chamber 120 to form the nitric oxide gas 126**.

Figure 5:
FIG. 5 is a top view of another exemplary nitric oxide (NO) delivery bandage, in accordance with the principles of the present disclosure.
Figure 5:
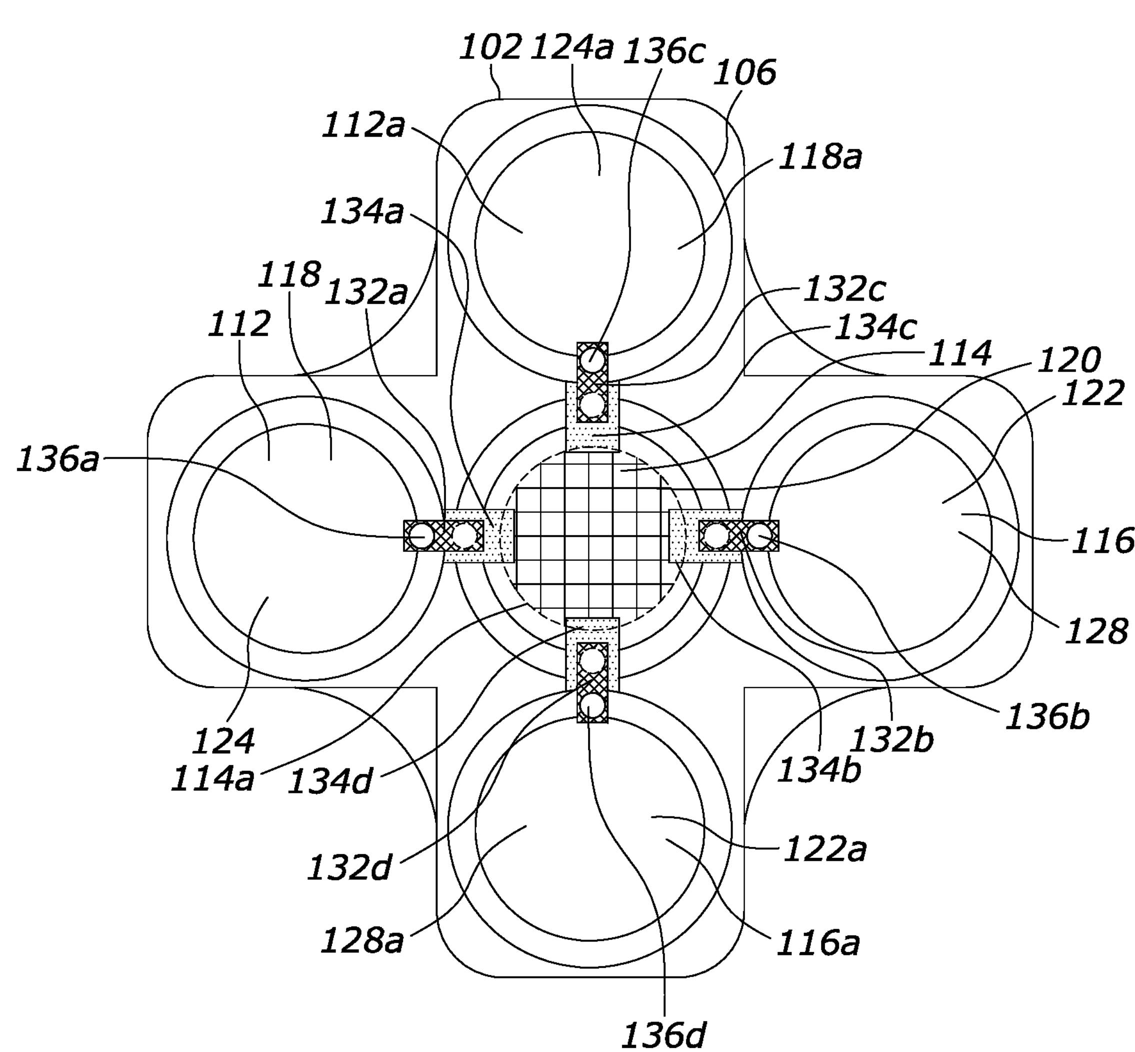

In other implementations, the NO bandage 100 may include four bubbles and chambers as shown in FIG. 5. In such an implementation, the NO bandage 100, in addition to the features shown and described in FIGS. 2A-2D, may include a fourth bubble **112*a* defining a fourth chamber 118*a* and a fifth bubble 116*a* defining a fifth chamber 122*a*. The fourth chamber 118*a* may contain a third mixture 124*a*, which may be the same as the mixture 124. The fifth chamber 122*a* may contain a fourth mixture 128*a*, which may be the same as the mixture 128. The fourth chamber 118*a* may be accessible to the mixing chamber 120 via passages 132*c*, 134*c* and a third plug 136*a*. The fifth chamber 122*a* may be accessible to the mixing chamber 120 via passages 132*d*, 134*d* and a fourth plug 136*d*. In operation, the fourth and fifth chambers 118*a*, 122*a* may include reserve mixtures 124*a*, 128*a*, respectively, such that a user may first initiate a mixing of the mixtures 124, 128 of the first and third chambers 118, 122 in the mixing chamber 120, and subsequently initiate a mixing of the reserve mixtures 124*a*, 128*a* of the fourth and fifth chambers 118*a*, 122*a*. The use of reserve mixtures and chambers may allow the user to keep the NO bandage 100 on the same desired location of skin for a longer period of time (e.g., 48 to 72 hours) while maintaining the therapeutic effect of the nitric oxide gas 126** during that time.

In some implementations, the NO bandage 100 may be incorporated into a fabric sleeve or other reusable device. In such implementations, the chambers of the NO bandage 100 may be refillable with suitable mixtures so that a user can keep the NO bandage 100 on the same desired skin location for a longer period of time.

Exemplary Test Setup

An exemplary NO bandage was built and tested to determine the NO production rate of the NO bandage by using both thumbs to press down on the outer chambers forcing the liquid in those chambers into the center mixing chamber. The outer chambers were alternatively depressed for 5 seconds, then the NO bandage was placed in an NO analyzer sample chamber to measure the NO production rate. When the NO concentration in the sample chamber was below 5 ppm, the next test was conducted.

Example 1

In the liquid/liquid version of the test, a citric acid solution was placed in the right chamber. A sodium nitrite solution was placed in the left chamber. When the outer chambers were depressed, the two solutions were forced into the middle mixing chamber where they mixed and produced NO gas.

Example 2

In the liquid/powder version of the test, sodium nitrite powder was placed in the center chamber. A citric acid solution was placed in both the right and left chambers. When the right and left chambers were depressed, the citric acid solutions were forced into the center mixing chamber where it came into contact with the powdered sodium nitrite and produced NO gas.

Additional aspects of the present disclosure may be embodied in other specific forms without departing from its fundamental functions or essential characteristics of this disclosure. The described embodiments are to be considered in all respects only as illustrative, and not restrictive. All changes which come within the meaning and range of equivalency of the illustrative embodiments are to be embraced within their scope.

The invention claimed is:

1. An adhesive bandage for delivering nitric oxide gas to skin, comprising:

a first chamber containing a first mixture;

a second chamber containing a second mixture that, when mixed with the first mixture, forms nitric oxide gas;

a mixing chamber disposed between the first chamber and the second chamber and configured to receive the first mixture and the second mixture to form nitric oxide gas; and a bandage layer configured to adhere to the skin, wherein the bandage layer includes an adhesive portion configured to prevent the nitric oxide gas from contacting ambient air.

2. The adhesive bandage of claim 1, wherein the first chamber is connected to the mixing chamber by a first rupturable gateway.

3. The adhesive bandage of claim 2, wherein the second chamber is connected to the mixing chamber by a second rupturable gateway.

4. The adhesive bandage of claim 3, wherein when fingertip pressure is applied to the first and second chambers, the first and second gateways rupture, allowing for mixing of the contents of the first and second chambers in the mixing chamber to form nitric oxide gas.

5. The adhesive bandage of claim 1, further comprising a fourth chamber containing a third mixture that is the same as the first mixture and a fifth chamber containing a fourth mixture that is the same as the second mixture.

6. The adhesive bandage of claim 5, wherein the bandage layer includes a membrane configured to diffuse the nitric oxide gas from the mixing chamber to the skin.

7. The adhesive bandage of claim 6, wherein the membrane allows only nitric oxide gas to pass through the membrane.

8. The adhesive bandage of claim 1, wherein the first chamber is connected to the mixing chamber by a first passageway including a first plug.

9. The adhesive bandage of claim 8, wherein the second chamber is connected to the mixing chamber by a second passageway including a second plug.

10. The adhesive bandage of claim 9, wherein when fingertip pressure is applied to the first and second passageways, the first and second plugs move toward the mixing chamber, allowing for mixing of the contents of the first and second chambers in the mixing chamber to form nitric oxide gas.

11. An adhesive bandage for delivering nitric oxide gas to skin, comprising:

a first chamber containing a first mixture;

a second chamber containing a second mixture that, when mixed with the first mixture, forms nitric oxide gas;

a mixing chamber disposed between the first chamber and the second chamber and configured to receive the first mixture and the second mixture to form nitric oxide gas, whereby the mixing chamber is formed of a flexible material that flexes in response to the nitric oxide gas expanding within the mixing chamber; and a bandage layer disposed underneath the first, second, and mixing chambers, the bandage layer including a membrane configured to diffuse the nitric oxide gas from the mixing chamber to the skin.

12. The adhesive bandage of claim 11, wherein the first chamber is connected to the mixing chamber by a first rupturable gateway.

13. The adhesive bandage of claim 12, wherein the second chamber is connected to the mixing chamber by a second rupturable gateway.

14. The adhesive bandage of claim 13, wherein when fingertip pressure is applied to the first and second chambers, the first and second gateways rupture, allowing for mixing of the contents of the first and second chambers in the mixing chamber to form nitric oxide gas.

15. The adhesive bandage of claim 11, wherein the membrane allows only nitric oxide gas to pass through the membrane.

16. The adhesive bandage of claim 11, wherein the first chamber is connected to the mixing chamber by a first passageway including a first plug.

17. The adhesive bandage of claim 16, wherein the second chamber is connected to the mixing chamber by a second passageway including a second plug.

18. The adhesive bandage of claim 17, wherein when fingertip pressure is applied to the first and second passageways, the first and second plugs move toward the mixing chamber, allowing for mixing of the contents of the first and second chambers in the mixing chamber to form nitric oxide gas.

19. A method for creating an adhesive bandage for delivering nitric oxide gas to skin, comprising:

providing a filling block including a first cavity, a second cavity, and a third cavity;

providing a membrane layer over the filling block, the membrane layer including a first chamber disposed in the first cavity, a second chamber disposed in the second cavity, and third chamber disposed in the third cavity;

filling the first cavity with a first mixture; and filling the third cavity with a second mixture, wherein the first mixture, when mixed with the second mixture in the second chamber, forms nitric oxide gas.

20. The method of claim 19, further comprising:

applying a transmission layer to the membrane layer;

applying a bandage layer to the membrane layer to create the adhesive bandage; and removing the adhesive bandage from the filling block.

* * * * *